US00PP13119P2

(12) United States Plant Patent
Pieters et al.

(10) Patent No.: US PP13,119 P2
(45) Date of Patent: Oct. 22, 2002

(54) GUZMANIA PLANT NAMED 'SOLANO'

(76) Inventors: Luc Pieters, Koewegstraat 4, 9270 Laarne (BE); Caroline De Meyer, Koewegstraat 4, 9270 Laarne (BE)

( * ) Notice: Subject to any disclaimer, the term of this patent is extended or adjusted under 35 U.S.C. 154(b) by 0 days.

(21) Appl. No.: 09/904,655

(22) Filed: Jul. 16, 2001

(51) Int. Cl.[7] ..... A01H 5/00
(52) U.S. Cl. ..... Plt./371

(58) Field of Search ..... Plt./371

*Primary Examiner*—Kent L. Bell
(74) *Attorney, Agent, or Firm*—Foley & Lardner

(57) ABSTRACT

A new and distinct Guzmania plant named 'Solano' characterized by having bright yellow bracts, with contrasting green tips; dark green upperside leaf color RHS 147A to 137A; light green underside leaf color RHS 146A to 138A; stiff, leathery leaf blade with a glossy surface; 4–6 branch spikes, each containing approximately 10 flowers; and approximately 60 flowers or flower buds present.

1 Drawing Sheet

BOTANICAL CLASSIFICATION

Guzmania hybrid.

VARIETY DENOMINATION

'Solano'.

BACKGROUND OF THE INVENTION

The present invention relates to a new and distinct cultivar of Guzmania. A genus within the family bromeliaceae, hereinafter referred to by the, cultivar name 'Solano'.

The new cultivar is a mutation discovered among a tissue culture derived group of Guzmania plant named 'Wendy'. Guzmania comprise a genus of over 100 species of herbaceous evergreen perennials suitable for cultivation in home or under glass. Guzmania, native to tropical America, are predominantly epiphytic with a few terrestrial species.

The species vary in diameter from 7 to 8 inches to 3 or 4 feet and have rosettes of glossy, smooth edged leaves. Floral bracts of Guzmania frequently have brillant colors and may last for many months. The range of flower colors for Guzmania is generally from the yellow through orange but may also include flame red and red purple. White or yellow, tubular, three-petalled flowers may also appear on a stem or within the leaf rosette but are usually short lived. Guzmania may be advantageously grown as potted plants for greenhouse or home use.

Desirably the plants are shaded from direct sunlight during the spring to autumn period, the central vase-like part of the leaf rosette is normally filled with water.

Guzmania leaves are usually formed as basal rosettes which are stiff and entire and in several ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in a appropriate soil or bark mixture. The new cultivar is a mutation discovered by the inventors, Luc Pieters and Caroline De Meyer, in Laarne, Belgium. The new cultivar was asexually propagated by off-shoots by the inventors in Laarne, Belgium.

The new variety has also been asexually reproduced by the inventors in Laarne, Belgium, by means of tissue culture. Continuous asexual propagation has demostrated that the combination of characteristics as herein disclosed for the new cultivar are firmly fixed and are retained through successive generations of asexual reproduction. The new cultivar reproduces true to type.

BRIEF DESCRIPTION OF THE INVENTION

The following traits have been repeatedly observed and are determined to be basic characteristics of 'Solano' which in combination distinguish this Guzmania as a new and distinct cultivar:

1. Bright yellow bracts, with contrasting green tips;

2. Dark green upperside leaf color RHS 147A to 137A; light green underside leaf color, RHS 146A to 138A;

3. Stiff, leathery leaf blade with a glossy surface;

4. 4–6 branch spikes, each containing approximately 10 flowers; and

5. Approximately 60 flowers or flower buds present.

'Solano' can be readily distinguished from other Guzmania hybrids by its known to the inventors bract color. 'Solano' is similar to the cultivar 'Wendy' (Unpatented) in all respects, except for the color of the leaves and the bracts of the inflorescence. Guzmania 'Wendy' is characterized by it dark red inflorescence. Compared to 'Wendy', the bracts of 'Solano' are bright yellow, with contrasting green tips.

'Solano' has not been tested under all available environmental conditions and the phenotype may vary with variations in environmental conditions such as temperature, light intensity, day length and humidity without however, any variance in genotype.

BRIEF DESCRIPTION OF THE DRAWING

The accompanying color photographic drawing shows typical characteristics of 'Solano' with colors being as true as possible with illustrations of this type. The photographic drawing shows a 12 month old plant of Guzmania 'Solano' grown from tissue culture, and finished in a 15 cm pot.

DETAILED BOTANICAL DESCRIPTION

The plant was grown in Laarne, Belgium, in greenhouse conditions which are typical of the industry. The plant described is 12 months old. Color references are made to The Royal Horticultural Society Colour Chart (R.H.S.), except where colors of ordinary significance are used.

Parentage: Mutation derived from Guzmania 'Wendy'.
Propagation: Tissue culture from off shoots.
Plant:
- *Form/growth habit.*—Basal Rosette, less densely layered, strap-like leaves arranged around a short central stem.
- *Height.*—Approximately 45 cm to 55 cm including inflorescence.
- *Diameter.*—Approximately 80–90 cm.

Foliage:
- *Leaf size.*—The basal leaves are approximately 48–55 cm long, and 5.5–6.0 cm wide(flattened); at their widest point near the base, the leaves are approximately 8.5 cm wide.
- *Leaf shape.*—The leaf blade is ligulate with an acute tip; the margins are entire; the leaves are curved outward over their length.
- *Surface texture.*—The leaf blade is stiff and leathery, with a glossy surface.
- *Color.*—The leaves are green throughout the foliage; the upperside has darker green color RHS 147A to 137A; the underside of the leaves are light green RHS 146A to 138A.
- *Average number of leaves.*—The plant produces approximately 20 leaves before producing an inflorescence.
- *Roots.*—White, green, changing to brown, some yellow endings.

BRACTS

Floral bracts:
- *Length.*—The upper-most floral bracts are approximately 6.5 cm long.
- *Width.*—1 cm.
- *Color.*—RHS 145A at base becoming RHS 151A towards apex becoming RHS 147A to RHS 145A at apex (Both surfaces).
- *Number.*—Approximately 28.
- *Margin.*—Entire.
- *Apex.*—Acute.
- *Texture.*—Leathery, with a glossy surface, shiny, smooth.
- *General shape/arrangement.*—The bracts are lanceolate and are arranged in closely spaced vertical ranks along the inflorescence.

Primary bracts:
- *Length.*—The primary bracts which cover branch spikes are approximately 10–15.5 cm long.
- *Width.*—4.5 cm; the base of the primary bracts at the attachment point to the scape is approximately 6.5 cm wide.
- *Color.*—The color of the largest most colorful primary bracts is RHS 145A at base becoming yellow ranging from RHS 7A to RHS 9A to RHS 12A towards apex becoming RHS 147A to RHS 145A at apex (Both surfaces).
- *Number.*—Approximately 17.
- *Margin.*—Entire.
- *Apex.*—Acute.
- *Texture.*—Leathery, with a glossy surface, shiny, smooth.
- *General shape/arrangement.*—The bracts are lanceolate and are arranged in closely spaced vertical ranks along the inflorescence.

Scape bracts:
- *Length.*—16 cm to 28 cm.
- *Width.*—4.5 cm; the base of the scape bract at the attachment point to the scape is approximately 6–7 cm wide.
- *Color.*—Green RHS 147A over more of the half of the length, yellow-green at the base RHS 145A (Both surfaces).
- *Number.*—Approximately 6.
- *Margin.*—Entire.
- *Texture.*—Leathery, with a glossy surface, shiny, smooth.
- *General shape/arrangement.*—The bracts are lanceolate and are arranged in closely spaced vertical ranks along the inflorescence.

Scape:
- *Height.*—Approximately 46 cm.
- *Diameter.*—Approximately 12 mm.
- *Color.*—RHS 145A to RHS 145B.

Branch spikes: The infloresence contains 4–6 branch spikes which protrude from under primary bracts, each containing approximately 10 flowers. The bracts of the branch spikes are similar in color and dimension to the floral bracts.

Flowers:
- *Borne.*—Terminal in the inflorescence, and in branch spikes.
- *Individual flowers.*—Approximately 60 flowers or flower buds present, terminal in the inflorescence concealed under bracts.
- *Calyx.*—Gamosepalous, three sepals present approximately 2.5 cm long and 5 mm wide, color translucent pale yellow RHS 4D (Both surfaces).
- *Corolla.*—Gamopetalous, three petals present approximately 5 cm long and 0.5 cm wide, color yellow RHS 12A (Both surfaces).
- *Time of blooming.*—In mature plants, flowering begins approximately 13–16 weeks after induction, at any time of the year.
- *Duration of inflorescence.*—The inflorescence will hold its color approximately 6 months; individual flowers last 1 day, and the total duration of flowering is about 12 weeks.

Reproductive organs:
- *Ovary.*—Superior, three locules, 8 mm long, colors RHS 145D, 4C, and 4D.
- *Style.*—3.2 cm long, colors RHS 145D, 4C, and 3D.
- *Stamens.*—6 present, filament approximately 4 cm long.
- *Anthers.*—5.2 mm long, color RHS 4D.
- *Pistils.*—One per flower.

Seed characteristics: Not observed.
Disease/pest resistance/susceptibility: No observations made to date.

We claim:

1. A new and distinct cultivar of Guzmania plant named 'Solano' as herein illustrated and described.

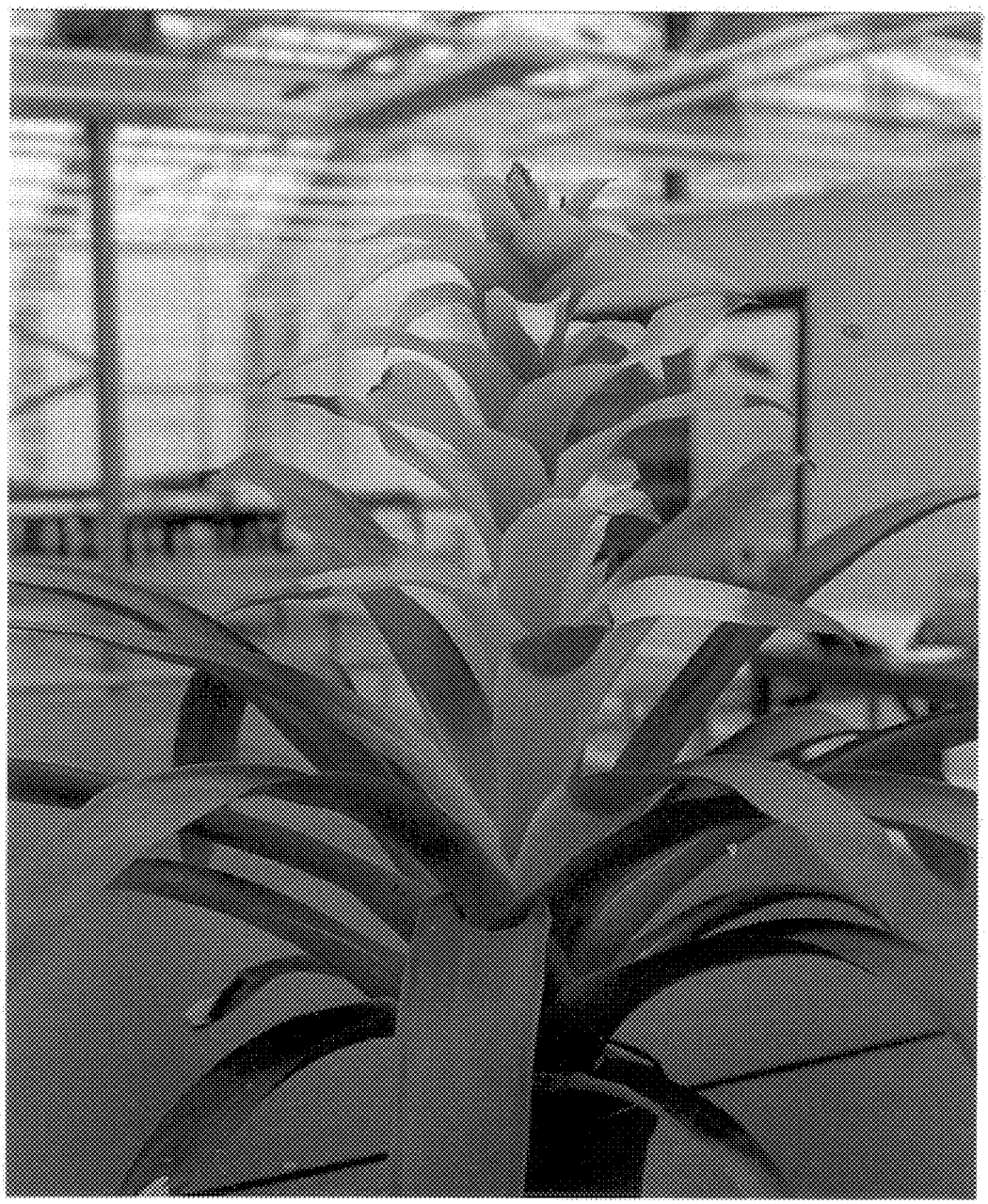

* * * * *